United States Patent [19]

Molter et al.

[11] 4,350,674

[45] Sep. 21, 1982

[54] SUBSTITUTED ACETANILIDOIMINODIACETIC ACID COMPOUNDS, DIAGNOSTIC AGENTS CONTAINING SUCH COMPOUNDS LABELED WITH TECHNETIUM-99M, AND METHODS FOR MAKING AND USING SUCH COMPOUNDS AND AGENTS

[75] Inventors: Michael Molter, Frankfurt am Main; Gerhard Kloss, Kelkheim, both of Fed. Rep. of Germany

[73] Assignee: Hoechst Aktiengesellschaft, Frankfurt am Main, Fed. Rep. of Germany

[21] Appl. No.: 150,573

[22] Filed: May 16, 1980

[30] Foreign Application Priority Data

May 18, 1979 [DE] Fed. Rep. of Germany ....... 2920174

[51] Int. Cl.$^3$ ..................... A61K 49/00; A61K 43/00
[52] U.S. Cl. ......................................... 424/1; 424/1.5; 424/9; 564/54; 564/194
[58] Field of Search ................ 424/1, 1.5, 9; 260/433, 260/571; 564/53, 54, 163, 164, 187, 442, 194

[56] References Cited

U.S. PATENT DOCUMENTS

| | | | |
|---|---|---|---|
| 3,740,418 | 6/1973 | Rajamani et al. | 424/1 |
| 4,013,716 | 3/1977 | Abblard et al. | 564/53 |
| 4,017,596 | 4/1977 | Loberg et al. | 424/1 |
| 4,058,557 | 11/1977 | Douglas et al. | 564/54 |

FOREIGN PATENT DOCUMENTS

2353299 12/1977 France ................... 424/1

OTHER PUBLICATIONS

Ju et al., Chem. Abstracts, vol. 90, Jun. 4, 1979, abstract #182407b.
Loberg et al., J. Nuc. Med., vol. 17, #7, Jul. 1976, pp. 633–638.
J. Labelled Compounds and Radiopharmaceuticals, vol. XVIII, Nos. 1–2 (1981), pp. 56–58.
Hauser et al., Radiology 94, 679–684 (1970).

*Primary Examiner*—Christine M. Nucker
*Attorney, Agent, or Firm*—Curtis, Morris & Safford

[57] ABSTRACT

What are disclosed are (2,3,4,5,6-pentafluoroacetanilido)-iminodiacetic acid and a method for its preparation from chloroacetic acid (2,3,4,5,6-pentafluoroanilide); (4-n-pentylacetanilido)-iminodiacetic acid and a method for its preparation from chloroacetic acid (4-n-pentylanilide); diagnostic agents for visualizing the heptobiliary system containing these substituted acetanilidoiminodiacetic acid compounds labeled with technetium-99m; and methods for making and using such diagnostic agents.

22 Claims, No Drawings

SUBSTITUTED ACETANILIDOIMINODIACETIC ACID COMPOUNDS, DIAGNOSTIC AGENTS CONTAINING SUCH COMPOUNDS LABELED WITH TECHNETIUM-99M, AND METHODS FOR MAKING AND USING SUCH COMPOUNDS AND AGENTS

The present invention relates to a novel product for the scintigraphic visualization of the hepatobiliary system (liver, gallbladder, intra- and extrahepatic biliary tract). The product is especially suitable for dynamic examinations.

Technetium-99m has prevailed lately in nuclear medical diagnosis because of its favorable physical parameters (no corpuscular radiation, gamma-radiation energy of 140 keV, half-life of 6 hours) and thus low radiation stress for patients and personnel, and because of its simple preparation by means of nuclide generators.

Technetium-99m obtained from such generators is first present in the form of pertechnetate, and it is suitable in this form for scintigraphy of the thyroid gland and the brain. In order to make feasible a Tc-99m-diagnosis of other organs, too, there have been developed organo-specific vehicular substances which can be easily labelled with Tc-99m and thus enable a good scintigraphic visualization of most different organs. For example, the RES-containing organs such as liver and spleen are well visualized by means of labelled colloids; suitable for bone scintigraphy are defined labelled phosphorus compounds, and so on.

For providing the vehicular substances with a Tc-99m label, the non-reacting pertechnetate ($TcO_4^-$) is first reduced to a lower oxidation state. In this form, technetium is reactive and forms relatively stable complexes with the corresponding vehicular substances.

$TcO_4^-$ can be reduced by chemical reducing agents or by electrolysis, reduction by means of tin(II) salts being, however, preferred nowadays.

Reduction with tin(II) is advantageous in that the reducing agent and the organo-specific vehicular substance—generally in freeze-dried form—can be stored together in a vial, so that in the hospital only the generator eluate containing the $^{99m}Tc$ pertechnetate has to be added in order to obtain the ready-to-use product.

Nuclear medical diagnosis, due to the detectors available, was limited for a long time to the localization of defined organs and the detection of their alterations. Because of improvements of detectors (gamma-camera) and their connection with electronic data processing systems, it has become possible to picture scintigrams in intervals of seconds and to record them. Such scintigram sequences not only permit the visualization of a defined organ, for example the liver, but also the collection of evidence on the function thereof, and is therefore called "function scintigraphy".

In a first stage, I-131-labelled substances capable of passing through the liver, such as $^{131}I$-rose bengal or bromosulfaleine-(I-131) were used for liver function studies. Because of the relatively high radiation dose and the relatively slow passage of these compounds through the liver, which is disadvantageous with respect to examination purposes, attempts were made to find a diagnostic agent capable of binding Technetium-99m for these examinations which passes the liver more rapidly.

According to the literature, mainly three different substances or classes of substances have been proposed for these examinations:
1. $^{99m}Tc$-Penicillamine [e.g. G. T. Krishnamurathy, M. Tubis, J. S. Endow et al., J. Nucl. Med. 13, 447 (1972)].
2. $^{99m}Tc$-Pyridoxalamino acids, especially $^{99m}Tc$-pyridoxalglutamate [e.g. R. J. Baker, J. C. Bellen, P. M. Ronai, J. Nucl. Med. 16, 720 (1975)].
3. $^{99m}Tc$-Acetanilido-iminodiacetate [e.g. E. Harvey, M. Loberg, M. Cooper: J. Nucl. Med. 16, 533 (1975)].

Thus, $^{99m}Tc$-(2,6-dimethylacetanilido)-iminodiacetate (HIDA) and $^{99m}Tc$-(2,6-diethylacetanilido)-iminodiacetate (EHIDA) were used.

In British Pat. No. 1,545,427, compounds of the formula

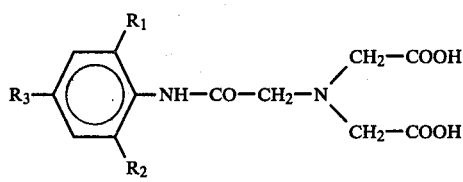

are described "in which at least two of the symbols $R_1$, $R_2$ and $R_3$ are lower alkyl groups having from 1 to 4 carbon atoms and the three symbols represent in total at least three carbon atoms". Verbatim, (2,6-diethylacetanilido)-iminodiacetate, (2,6-diisopropylacetanilido)-iminodiacetate and (2,4,6-trimethylacetanilido)-iminodiacetate are mentioned.

A certain amount of all derivatives of acetanilidoiminodiacetate hitherto described is excreted via the kidney, so that the kidney, too, is distinctly visualized.

The present invention provides a process for the manufacture of a diagnostic agent for liver function diagnosis, which agent is excreted via the kidney to an insignificant extent only: for a satisfactory absorption of the diagnostic agent in the liver in patients suffering from a limited liver function can be expected only if the compensatory excretion via the kidneys is low.

A feature of the present invention is a process for the preparation of a diagnostic agent for liver function studies, which agent is excreted via the kidneys in extremely small amounts, which comprises mixing (2,3,4,5,6-pentafluoro-acetanilido)-iminodiacetic acid (PFIDA) or (4-n-pentylacetanilido)-iminodiacetic acid (PIDA) in aqueous solution with a tin(II) salt, in a molar ratio of from 10:1 to 200:1, adjusting the pH of the solution to a value between 4 and 9, preferably between 5.5 and 6.5, and subsequently adding from 0.1 to 100 mCi of Tc-99m pertechnetate in a physiological saline solution, depending on the intended purpose. The concentration of PFIDA and PIDA, respectively, is preferably in the range of from 0.1 to 200 mg/ml, preferably between 10 and 50 mg/ml of the stock solution.

The concentration of tin(II) salt is advantageously in the range of from 0.01 to 5 mg/ml, preferably of from 0.1 to 0.5 mg/ml, of stock solution.

Suitable tin(II) salts, by way of example, are $SnF_2$, $SnSO_4$, Sn-tartrate, SnO, Sn-oxalate or other tin(II) salts, chlorides, in particular $SnCl_2.2H_2O$ being preferred.

For preparing the diagnostic agent it is advantageous to dissolve the (2,3,4,5,6-pentafluoroacetanilido)-iminodiacetic acid in water with addition of aqueous sodium hydroxide solution. NaOH is added in an amount required for the complete dissolution of the compound. The pH after this dissolution is from 7 to 10; and it is then adjusted to about 5 with HCl. Subsequently, the corresponding amount of Sn(II) salt (dissolved in 0.1 N HCl) is added, the batch is agitated for 30 minutes under a protecting gas atmosphere, and the pH is adjusted to 6.

By adding Technetium-99m pertechnetate, this solution can be used within 24 hours as a ready-to-use diagnostic agent. On the other hand, it may be frozen or lyophilized for storage purposes. The lyophilized product is stable for at least 8 months under a protecting nitrogen atmosphere.

Frequently the solution obtained according to the process of the invention is combined with Technetium-99m-pertechnetate at a later stage. In this case, the solution is suitably divided into equal portions, for example by dispensing it to suitable vials such as beaded rim vials, for example in portions of 1 or 2 ml. The solution is subsequently frozen or lyophilized. A labelling unit is obtained in this manner containing of from 1 to 200 mg, preferably of from 10 to 50 mg, of PFIDA or PIDA and of from 0.01 to 5 mg, preferably of from 0.1 l to 0.5 mg, of tin(II) salt. Prior to use, of from 0.1 to 100 mCi, preferably of from 1 to 10 mCi, of technetium-99m-pertechnetate in 1 to 10 ml of pertechnetate solution, per patient, is added to the labelling unit.

Generally, the ready-to-use diagnostic agent, which contains from one fifth to one labelled unit, is administered to a patient intravenously.

A further feature of the present invention is furthermore a diagnostic agent for visualizing the hepatobiliary system, which agent comprises Technetium-99m-labelled (2,3,4,5,6-pentafluoroacetanilido)iminodiacetate or (4-n-pentylacetanilido)iminodiacetate in a physiological saline solution.

As compared to known products, the novel diagnostic agent is distinguished by a greatly decreased activity concentration in the kidneys and by a reduced excretion into the bladder. These advantages are demonstrated in the following animal tests:

(1) 0.5 mCi of the corresponding labelled diagnostic agent is administered to a rabbit by injection into the ear vein, and the distribution of the activity is observed in its temporal course by means of a gamma-camera connected with a data processing system. With all of the known products the kidneys have been visualized, while with the novel diagnostic agents PFIDA and PIDA they cannot be localized practically.

(2) Portions of 30 μCi of the respective diagnostic agent are administered to groups of 12 rats, whose efferent urinary tract has been ligatured for determination of the activity in the urinary bladder, by injection into the femoral vein. Subsequently, 3 animals are killed after 5, 10, 20 and 30 minutes, respectively, and the distribution of radioactivity in the organs is determined. The results are listed in the following table:

| Substitution in the benzene ring | time | liver % | intestines % | kidneys % | bladder % |
|---|---|---|---|---|---|
| 2,6-dimethyl- (HIDA) | 5' | 21.7 | 43.2 | 7.4 | 0.9 |
| | 10' | 9.6 | 65.9 | 7.4 | 1.7 |
| | 20' | 2.2 | 80.8 | 5.8 | 2.3 |
| | 30' | 1.0 | 79.7 | 4.9 | 2.8 |
| 2,6-diethyl- (EHIDA) | 5' | 6.9 | 71.2 | 4.3 | 0.4 |
| | 10' | 3.4 | 79.9 | 4.2 | 1.3 |
| | 20' | 1.6 | 81.7 | 3.6 | 1.6 |
| | 30' | 1.5 | 81.8 | 3.4 | 1.8 |
| 2,3,4,5,6-pentafluoro- (PFIDA) | 5' | 28.3 | 35.6 | 2.4 | 0.8 |
| | 10' | 14.1 | 64.8 | 2.5 | 1.1 |
| | 20' | 5.8 | 78.3 | 1.7 | 1.7 |
| | 30' | 3.8 | 81.8 | 1.6 | 1.8 |
| 4-n-pentyl-IDA (PIDA) | 5' | 65.6 | 24.6 | 1.0 | 0.04 |
| | 10' | 46.5 | 46.9 | 1.0 | 0.05 |
| | 20' | 22.2 | 73.4 | 1.1 | 0.09 |
| | 30' | 12.5 | 85.4 | 1.0 | 0.13 |

The excretion of activity into the bladder, especially with the compound PIDA, is negligible.

EXAMPLE 1

Manufacture of (2,3,4,5,6-pentafluoroacetanilido)iminodiacetic acid

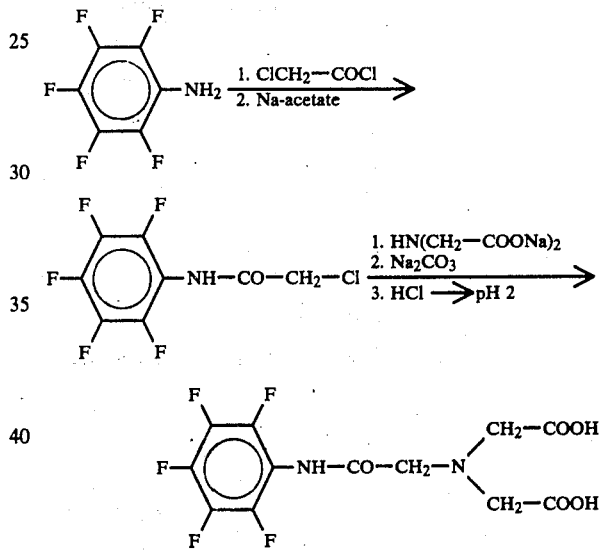

(a) 18.31 g (0.1 mol) of 2,3,4,5,6-pentafluoroaniline are dissolved in 80 ml of glacial acetic acid. The solution is cooled to 10° C., 12.4 g (0.11 mol) of chloroacetic acid chloride are added, and the batch is thoroughly intermixed. Subsequently, 100 ml of semi-saturated aqueous sodium acetate solution and 100 ml of water are added with thorough agitation, and agitation is continued for a further 30 minutes. The chloroacetic acid-(2,3,4,5,6-pentafluoroanilide) precipitated is suction-filtered and recrystallized from methanol.

Melting point: 139°–141° C.

Elementary analysis:

| | C | H | N | Cl |
|---|---|---|---|---|
| calc. | 37.02% | 1.16% | 5.40% | 13.66% |
| found | 37.0% | 1.3% | 5.6% | 13.7% |

NMR (in DMSO-$d_6$, internal standard: TMS): —CH—: δ=4.37 ppm(s); —NH—:δ=10.42 ppm(s).

(b) 4.0 g (22 mmols) of iminodiacetic acid disodium salt, 5.7 g (20 mmols) of $Na_2SO_3 \cdot 10H_2O$ and 5.2 g (20 mmols) of chloroacetic acid-(2,3,4,5,6-pentafluoroanilide) are added to 60 ml of water and 30 ml of ethanol, and the batch is refluxed for 24 hours. After cooling, the solvent is removed and the residue is dissolved in about 150 ml of water. This aqueous solution is washed 4 times with about 50 ml of diethyl ether and subsequently the pH is slowly adjusted to 2 with HCl. The precipitated product is suction-filtered and again dissolved in water with addition of such an amount of NaOH which is required to dissolve the substance completely. After filtration, (2,3,4,5,6-pentafluoroacetanilido)-iminodiacetic acid is precipitated again by adding HCl until the pH is adjusted at 2, suction-filtered and dried.

Melting point: 181°–184° C.

Elementary analysis:

|  | C | H | N |
|---|---|---|---|
| calc. | 40.46% | 2.55% | 7.86% |
| found | 40.7% | 2.8% | 7.8% |

NMR (in DMSO-$d_6$, int. standard: TMS): $>$N—CH$_2$—COOH:$\delta$=3.56 ppm(s); —CO—CH$_2$—N$<$:$\delta$=3.61 ppm(s); —NH— —COOH}:$\delta\approx$11.5 ppm(s)+).

+) As a result of the fluorine substitution in the benzene ring, the NH proton is acidified to such an extent that a rapid exchange with the water present in the solvent and with the acid protons occurs. Therefore only one signal characterized by an average chemical shift is observed.

EXAMPLE 2

(4-n-Pentylacetanilido)iminodiacetic acid is obtained by synthesis from 4-n-pentylaniline by way of chloroacetic acid(4-n-pentylanilide) as an intermediate, as in Example 1. The following physical data are found:

Melting point: 192°–194° C.

Elementary analysis:

|  | C | H | N |
|---|---|---|---|
| calc. | 60.70% | 7.19% | 8.33% |
| found | 61.0% | 7.0% | 8.2% |

NMR (in DMSO-$d_6$; internal standard: TMS): $>$N—CH$_2$—COOH:$\delta$=3.55 ppm(s); —CO—CH$_2$—N:$\delta$=3.47 ppm(s); —NH$<$:$\delta$=10.13 ppm(s); —COOH:$\delta$=12.5 ppm(s, broad); aromatic protons (A$_2$B$_2$-system):$\delta_A$=7.11 ppm; J$_{AB}$=8 Hz; $\delta_B$=7.50 ppm; —CH$_2$—($\alpha$):$\delta$=2.54 ppm (t); J=7 Hz; —(CH$_2$-)$_3$—($\beta$—$\delta$):$\delta$=1.0–1.7 ppm (m); —CH$_3$($\epsilon$):$\delta$=0.86 ppm (t); J=6 Hz.

EXAMPLE 3

7 g of (2,3,4,5,6-pentafluoroacetanilido)-iminodiacetic acid are dissolved in 100 ml of 1 N sodium hydroxide solution, and 70 mg of SnCl$_2$.2H$_2$O (dissolved in 7 ml of 0.1 N hydrochloric acid) are added. After stirring for 5 minutes, the pH is adjusted to 6 by means of hydrochloric acid, the batch is completed to 233 ml, dispensed in portions of 1 ml each to beaded rim vials, and frozen with liquid nitrogen. Subsequently and the product is lyophilized, the vials are filled with nitrogen and closed. After a storage time of 60 days, 0.3 mCi of Tc-99m pertechnetate in 10 ml of physiological saline solution is injected into the closed vials. For the purpose of animal tests, 0.5 ml each of the diagnostic agent so obtained is administered intravenously to rats after a reaction time of about 30 minutes (typical test results are indicated in the table as shown on page 6).

EXAMPLE 4

1 N NaOH is added to an aqueous suspension of 3 g of (4-n-pentylacetanilido)iminodiacetic acid in about 60 ml of water in an amount sufficient for complete dissolution of the acid and subsequently 20 mg of SnF$_2$ (dissolved in 5 ml of 0.1 N hydrochloric acid) are added. After stirring for about 10 minutes, the pH is adjusted to 6 and the batch is completed to 100 ml. The solution is dispensed to beaded rim vials in 1 ml portions and frozen with liquid nitrogen. Subsequently and the product is lyophilized, the vials are filled with nitrogen and then closed.

After a time of storage between 1 day and 15 months, the labelling unit is rendered ready for injection. For the purpose of animal tests, the solution so obtained is administered to rats (typical test results are listed in the table as shown on page 6).

What is claimed is:

1. Chloroacetic acid (2,3,4,5,6-pentafluoroanilide).

2. A method for making the compound of claim 1 which comprises reacting 2,3,4,5,6-pentafluoroaniline with chloroacetic acid chloride.

3. (2,3,4,5,6-pentafluoroacetanilido)-iminodiacetic acid or a salt thereof.

4. A method for making (2,3,4,5,6-pentafluoroacetanilido)-iminodiacetic acid which comprises reacting chloroacetic acid (2,3,4,5,6-pentafluoroanilide) with iminodiacetic acid in an alkaline medium to form a (2,3,4,5,6-pentafluoroacetanilido)-iminodiacetate and recovering the free acid therefrom.

5. A diagnostic agent for visualizing the heptobiliary system, which agent comprises a physiological saline solution of (2,3,4,5,6-pentafluoroacetanilido)-iminodiacetic acid labelled with technetium-99m.

6. A method for visualizing the heptobiliary system of a patient for purposes of scintigraphic examination, which method comprises intravenously administering to said patient an amount, effectively detectable by scintigraphy, of a diagnostic agent as in claim 5.

7. Chloroacetic acid (4-n-pentylanilide).

8. A method for making the compound of claim 7 which comprises reacting 4-n-pentylaniline with chloroacetic acid chloride.

9. (4-n-pentylacetanilido)-iminodiacetic acid or a salt thereof.

10. A method for making (4-n-pentylacetanilido)-iminodiacetic acid which comprises reacting chloroacetic acid (4-n-pentylanilide) with iminodiacetic acid in an alkaline medium to form a (4-n-pentylacetanilido)-iminodiacetate and recovering the free acid therefrom.

11. A diagnostic agent for visualizing the heptobiliary system, which agent comprises a physiological salt solution of (4-n-pentylacetanilido)-iminodiacetic acid labelled with technetium-99m.

12. A method for visualizing the hepatobiliary system of a patient for purposes of scintigraphic examination, which method comprises intravenously administering to said patient an amount, effectively detectable by scintigraphy, of a diagnostic agent as in claim 11.

13. A method for making a diagnostic agent for liver function studies, which method comprises preparing an aqueous solution of a tin (II) compound and member selected from the group consisting of (2,3,4,5,6-pentafluoroacetanilido-iminodiacetic acid (PFIDA) and (4-n-pentylacetanilido)-iminodiacetic acid (PIDA) in a molar ratio from 1:10 to 1:200, adjusting the pH of the aqueous solution to a value between 4 and 9, and adding a physiological saline solution containing from 0.1 l to 100 millicuries of technetium-99m.

14. A method as in claim 13 wherein said tin (II) compound is SnO, SnCl$_2$.2H$_2$O, SnSO$_4$, Sn-tartrate, Sn-oxalate, or Sn-acetate.

15. A method as in claim 13 wherein the concentration of PFIDA or PIDA in said agent is from 0.1 to 200 mg/ml.

16. A method as in claim 13 wherein the concentration of PFIDA or PIDA in said agent is from 10 to 50 mg/ml.

17. A method as in claim 13 wherein the pH of said aqueous solution is adjusted to a value between 5.5 and 6.5.

18. A method for making a labelling unit comprising a carrier for technetium-99m and adaptable for conversion to a diagnostic agent for visualizing the heptobiliary system by the addition thereto of a solution of technetium-99m, which method comprises preparing an aqueous solution of a tin (II) compound and a member selected from the group consisting of (2,3,4,5,6-pentafluoroacetanilido)-iminodiacetic acid and (4-n-pentylacetanilido)-iminodiacetic acid (PIDA) in a molar ratio from 1:10 to 1:200, adjusting the pH of the aqueous solution to a value between 4 and 9, dividing the aqueous solution into a plurality of portions each containing from 0.01 to 5 mg of said tin (II) compound and from 1 to 200 mg of PFIDA or PIDA, and lyophilizing said portions to provide a plurality of said labelling units.

19. A method as in claim 18 wherein said plurality of portions each containing from 0.1 to 0.5 mg of said tin (II) compound and from 10 to 50 mg of PFIDA or PIDA.

20. A method as in claim 18 wherein said pH is adjusted to a value between 5.5 and 6.5.

21. A method for making a diagnostic agent for liver function studies, which method comprises adding from 1 to 10 ml of a physiological saline solution containing from 0.1 to 100 milliCuries of technetium-99m pertechnetate to a labelling unit as in claim 18.

22. A method as in claim 21 wherein said saline solution contains from 1 to 10 milliCuries of technetium-99 pertechnetate.

* * * * *